(12) United States Patent
Coyle et al.

(10) Patent No.: US 11,883,007 B2
(45) Date of Patent: Jan. 30, 2024

(54) CONTROLLED MOTION CAPSULE

(71) Applicant: Brian Michael Coyle, Canyon, CA (US)

(72) Inventors: Brian Michael Coyle, Canyon, CA (US); Alys Larsen, Canyon, CA (US)

(*) Notice: Subject to any disclaimer, the term of this patent is extended or adjusted under 35 U.S.C. 154(b) by 0 days.

(21) Appl. No.: 17/825,515

(22) Filed: May 26, 2022

(65) Prior Publication Data
US 2023/0043450 A1 Feb. 9, 2023

Related U.S. Application Data

(60) Provisional application No. 63/230,699, filed on Aug. 7, 2021.

(51) Int. Cl.
*A61B 1/04* (2006.01)
*A61B 1/00* (2006.01)
*A61B 5/07* (2006.01)

(52) U.S. Cl.
CPC .......... *A61B 1/041* (2013.01); *A61B 1/00016* (2013.01); *A61B 5/073* (2013.01); *A61B 2560/045* (2013.01)

(58) Field of Classification Search
CPC ... A61B 1/041; A61B 1/00016; A61B 1/0661; A61B 1/0684; A61B 5/073; A61B 2560/045; A61B 2090/3945; A61F 2210/0047; A61N 5/06; A61N 2005/0651; A61N 2005/0653
See application file for complete search history.

(56) References Cited

U.S. PATENT DOCUMENTS

| | | | |
|---|---|---|---|
| 4,507,115 A * | 3/1985 | Kambara | A61M 31/002 604/93.01 |
| 7,201,511 B2 | 4/2007 | Moriyama et al. | |
| 7,552,702 B2 | 6/2009 | Stone | |
| 8,684,010 B2 | 4/2014 | Shachar et al. | |
| 9,283,044 B2 | 3/2016 | Juloski et al. | |
| (Continued) | | | |

OTHER PUBLICATIONS

Yao, H., Stidham, R.W., Gao, Z., Gryak, J., Najarian, K., Motion-based camera localization system in colonoscopy videos, Medical Image Analysis, 2021, 73: 102180.
(Continued)

*Primary Examiner* — Timothy J Neal
*Assistant Examiner* — William B Chou

(57) ABSTRACT

Controlled motion capsules and associated systems and methods are described. Controlled motion capsules can decelerate, and stop, without damaging epithelial walls. If any components fail, a controlled motion capsule, without added energy, becomes its most compact shape, passing harmlessly through the GI tract. Controlled motion capsule may include a shape changing material, comprising a reversible soft copolymer, in a container in the capsule, with a nonionizing radiation emitter, and a controller to activate the nonionizing radiation to expand and contract the shape changing material, on detection of certain conditions or instructions. Expansion of the shape changing material, including contact with epithelial walls, decelerates and can stop the controlled motion capsule movement. Motion control allows scientists to study the microbiome, doctors to deliver intestinal drugs at precise locations, and to closely examine signs of precancerous growth.

20 Claims, 9 Drawing Sheets

(56) References Cited

U.S. PATENT DOCUMENTS

| | | | |
|---|---|---|---|
| 9,750,923 B2* | 9/2017 | Niichel | A61K 31/00 |
| 10,300,296 B2 | 5/2019 | Ben-Yehuda et al. | |
| 2005/0096712 A1* | 5/2005 | Abraham-Fuchs | A61B 34/73 607/89 |
| 2007/0123809 A1* | 5/2007 | Weiss | A61B 5/073 601/84 |
| 2008/0188837 A1* | 8/2008 | Belsky | A61K 9/0097 604/890.1 |

OTHER PUBLICATIONS

Vaidya, H., Makinde, O.D., Choudhari, R., Prasad, K.V., Khan, S.U., Vajravel, K., Peristaltic flow of non-Newtonian fluid through an inclined complaint nonlinear tube: application to chyme transport in the gastrointestinal tract, Eur. Phys. J. Plus, 2020, 135:934.

Bianchi, F., Masaracchia, A., Shojaei Barjeui, E., Menciassi, A., Arezzo, A., . . . Cuiti, G., Localization strategies for robotic endoscopic capsules: a review, Expert Review of Medical Devices, 2019, 16(5), 381-403.

Huda, M.N., Liu, P., Saha, C., Yu, H., Modelling and Motion Analysis of a Pill-Sized Hybrid Capsule Robot, Journal of Intelligent & Robotic Systems, 2020, 100:753-764.

Ams-OSRAM AG, "Thermal management of LED light sources" Application Note Document No. AN052 2 / 23 Aug. 18, 2022, Premstaetten, Austria.

Decter et al., "There's Something About Mark", Scene 61, Final Shooting Script, Oct. 21, 1997, p. 1, Copyright © 1998, 20th Century Fox, Los Angeles.

* cited by examiner

CONTROLLED MOTION CAPSULE

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

CROSS-REFERENCE TO RELATED APPLICATIONS

The present application claims benefit under 35 USC § 119(e) of U.S. Provisional Patent Application Ser. No. 63/230,699 filed on 7 Aug. 2021. The present application is based on and claims priority from this application, the disclosure of which is hereby expressly incorporated herein by reference.

BACKGROUND OF THE INVENTION

Swallowable endoscopic capsules, which move through the digestive system through the collective actions of digestion, present an alternative to the endoscopic cable probe and camera currently employed in the human health care field. The cable and camera systems demand patient sedation, cause patient discomfort, have potential risks, and are costly. Capsule systems can be used in out-patient settings, cause no discomfort, have little risk, and cost much less. But health care has extraordinary demands. Since their introduction 15 years ago, and despite advances in the field of miniaturization generally, there has been limited use of capsules for routine endoscopic investigation. It is not enough to be less expensive and less invasive. A health care solution must perform as well or better than existing solutions to change health care practice.

The motion of cable and camera endoscopic systems can be controlled by medical practitioners. They can decelerate motion of the device, including stopping it, to examine areas of the body where they detect a condition of interest. This also offers an incomplete degree of camera localization, necessary for diagnosis and prognosis of multiple diseases. Although sensors can increase the precision of absolute position determination, many gastroenterologists prefer the feasibility of estimating the relative position of the camera by measuring from the start of the colon. This is considered sufficient for contextual understanding of colon features (Yao, et al., 2021, 1.)

The control of motion of capsule endoscopes is currently limited. Their movement through the intestinal system is due to peristaltic flow, a non-linear process that varies according to fluid properties (viscosity, thermal volatility and conductivity), wall properties (dimension, absorbency), non-continuum slip flow, chemical actions, microbe distributions, and inclination. Groups of muscle fibers contract in the intestinal wall, squeezing solids and fluids forward towards an area where muscles are relaxed. Models of the system emphasize its nonlinear variability (Vaidya, et al. 2020, 2.)

As a force that propels capsule endoscopes, peristaltic flow does not promote locationization specificity. This is the limiting factor against capsule endoscope adoption.

There has been an effort to advance the use of swallowable endoscopic capsules, by increasing the control a medical investigator has of the capsule movement through the internal organs of a patient. Some methods attempt to simply locate the capsule accurately, rather than control its movement (Bianchi, et al. 2019, 3.) These do not provide the essential service offered by cable and camera endoscopes, which can decelerate and pause at locations of concern.

Several academic and industrial groups have investigated the use of magnetic field-based localization and locomotion strategies. U.S. Pat. No. 8,684,010 to Shachar et al. (P1) describes a magnetized capsule that is propelled and directed through the GI tract with external magnetic fields generated on a table the patient lays on. Its goal is to overcome the limitations of gastrointestinal motility and gravity for movement, the randomness of imagining, and inability to focus on a specific location. The external magnet solution is complex and difficult, since the intervening body tissue reduces magnetic forces, and the intestines are nonlinear, requiring the capsule to move through many degrees of freedom. The goal is to use magnetic fields for capsule steering and locomotion. Requiring a patient to lay on a special table requires in-patient services, highly trained staff, and has elevated costs. The magnetic fields required to adequately direct an internal capsule risk causing injury, particularly if the patient has a pacemaker or other medical device.

U.S. Pat. No. 9,283,044 to Siemens (P2) teaches a magnetically guided capsule endoscopy system that can be controlled by a medical professional, using a table under which a solenoid system emits magnetic fields. It is limited to investigating a patient's esophagus, stomach and optionally the duodenum with capsule endoscopy. Again, the purpose is to control the capsule's movement, namely to have it take a certain position. It has proved challenging to avoid interference between localization and locomotion modules.

Other methods have been tested to slow or pause capsule movement, such as external "arms," "hooks," and "claws" that rotate out from the capsule to rub against gastrointestinal [GI] tract walls (Huda, et al. 2020, 4.) The GI tract is filled with fluid and suspended solids, in a convoluted tubular system. This can impact plastic, composite, or metal appendages sticking out from the sides of a swallowable capsule, causing them to bend or break, or jam into the soft epithelial folds of side walls. Such devices have not been approved by FDA. Any device can fail, so all swallowable capsules must have a configuration that, in case of failure, permits them to safely pass through and out of the GI tract. A device with external elements, should the device fail to rotate or fold them back, presents an unacceptable health care risk.

As these efforts show, there is needed an efficient and effective swallowable capsule device for GI inspection and treatment that can be decelerated and stopped in a specific position in the GI tract, without heavy, dangerous magnetic machinery, without external elements that may break or lodge, without elements that may cause intestinal blockages. The need is exemplified by U.S. Pat. No. 10,300,296 to Ben-Yehuda (P3), which is a light-emitting capsule that tries to prevent the inevitable photodynamic damage that will happen when movement of a capsule that emits therapeutic radiation varies unpredictably within a GI tract. Because such capsules cannot adjust velocity, and may stall at any time, this device includes a speed determination unit, which is used to adjust or stop irradiation. This illustrates an effort to mitigate the limitations of lack of capsule motion control. It treats a by-product of swallowable capsule movement, rather than fixing the problem. Current cable and camera endoscopic systems can modify motion to inspect areas of concern. This is the threshold that must be achieved, safely, to achieve capsule success.

Only by pausing the movement of the capsule can careful examination occur, can accurate somalocation be determined, can precision therapy be provided. Within the domain of health care, devices must also fail safely. If capsule power, communication, control, or other attributes fail, rendering a capsule inoperable, the capsule must not become a health risk.

SUMMARY OF THE INVENTION

Embodiments of the invention provide devices, systems, and methods for visiting various tubular locations in the body. The embodiments provide a swallowable device that is a controlled motion capsule that contains a shape changing material such as a hydrogel or other gel-like media in a container, the shape changing material having the capacity to reversibly expand and contract on exposure to a nonionizing radiation that transmits one or a plurality of wavelengths (between 200 nm and 2,000 nm) and which may transmit thermal energy. Particular embodiments provide a swallowable device, in capsule form, for carrying out inspection of tubular structures in the human body, especially the GI tract, as well as delivering therapeutic agents therein. Embodiments provide a gel-like media in the capsule that swells and shrinks, and a membrane layer anterior to the gel-like media that correspondingly expands and contracts. Embodiments of the invention are useful for close inspection and medical investigation of the body's tubular structures, by decelerating the controlled motion capsule when the shape changing material expands when exposed to nonionizing radiation, and stopping when when the shape-changing material presses against the tubular structure's walls. Further embodiments of the invention can be used to deliver therapeutic treatments that require precise somalocation. The controlled motion capsule may have various optical, magnetic, rotational, accelerational, and other sensor signals, used to track its trajectory and determine somalocation.

In one aspect, the invention provides a swallowable device for inspection and treatment of the small or large intestine. The device is a controlled motion capsule that can be swallowed and pass through the GI tract. The controlled motion capsule includes an interior volume and can be made from various polymers known in the art. The controlled motion capsule can include at least one container sealed from other parts of the capsule, in which a gel-like media such as a hydrogel or liquid crystal elastomer is positioned, which can reversibly swell and shrink, or reversibly change from one shape to a different shape. Hydrogels are three-dimensional polymer networks that can swell due to hydration. Hydrogels have chemical or physical crosslinks. The crosslinks produce changes in hydrogel viscoelastic properties. Many hydrogels can reversibly swell and shrink in response to changes in external environmental stimuli, and those with physical crosslinks possess physical domain junctions, hydrogen bonding, hydrophobic interaction, and ionic complexation, facilitating fabrication and reshaping, and exhibit superior biodegradation and non-toxicity.

Hydrogels with different concentrations of water-soluble synthetic polymers exhibit different network structures, with different responses to light and temperature induced phase transitions. Light-responsive hydrogels include photopolymerizable hydrogels, where light adds crosslinks and/or biochemical cues, and photolabile hydrogels where light cleaves crosslinks and/or removes biochemical cues and/or caging compounds. Photo-sensitive molecules respond to light via several main mechanisms. This invention has embodiments that use isomerization or cyclization, degradation, and dimerization of constituent compounds. Embodiments include hydrogels tuned to optimize texture and wavelength response. Viscosity modifiers may be added to the media, such as carboxylic acids or polyhydric alcohols. Mechanical properties may be improved by interlacing multiple inseparable polymer networks that do not covalent bond with each other.

"Positive" light-responsive or thermo-sensitive hydrogels swell at high temperatures or under irradiation, and shrink at low temperatures or in the absence of light. "Negative" light-responsive or thermo-sensitive hydrogels swell at low temperatures or in the absence of light, and shrink at high temperatures or under irradiation. In this invention's embodiments, "positive" light-responsive or thermo-sensitive hydrogels are preferred, to provide a fail-safe mechanism for ensuring the device will shrink to a compact form should device components, such as energy sources or controls, fail. This is because when irradiation ceases, the "positive" hydrogel shrinks, and any surrounding membrane contracts. Such embodiments ensure the passage and excretion of the device through the GI tract.

An embodiment includes light-responsive hydrogels formed by incorporating spiropyran chromophores that are copolymerized with poly(N-isopropylacrylamide) and polyacrylic acids. Another embodiment forms copolymers of N,N-dimethylacrylamide (DMA) and methacryloyloxyazobenzene (MOAB) with pendant azobenzene chromophore moieties along the backbone. This embodiment may be controlled with light at 430-436 nm. Another embodiment uses hexaarylbiimidazole chromophores directly incorporated into polymer backbones by nonfree radical polymerization.

In general, an implementation generates macroscopic shape change of the material by incorporating molecular photoswitches such as spiropyrans, diarylethenes, hexaarylbiimidazoles, and azobenzenes into the polymer material, and initiating a photochemical reaction with light. Photoisomerization of molecules causes a generally reversible structural change between isomers by photoexcitation. Of the different photoisomerizers available, spiropyrans exhibit extraordinary sensitivity to photons, and are used in preferred embodiments of the invention. The spiropyran photochemical reaction involves dissociation of $C_{spiro}$—O bond followed by either relaxation back to a ring-closed form, or a twisting motion to a new geometry along the pi-electron dimension. It is used in embodiments where the reversibly swelling and shrinking gel-like media is a light-responsive, spiropyran-functionalized hydrogel that is reversibly photo-actuated.

Thermo-sensitive hydrogels can be synthesized from natural polymers (chitosan, cellulose, and gelatin) and synthetic polymers (poly[N-isopropylacrylamide] and polyfluorene). In an embodiment a gel-like media may comprise a reversible copolymer containing a derivatized acrylamide in an amount sufficient to cause a transition from a first state to a second state due to a temperature change of less than 25 degrees. The invention may employ coelectrospinning of precursor polymers to create cross-linked nanostructured hydrogels, that reversibly respond to temperature changes within seconds.

Light-activated hydrogel volume changes may be induced by light radiation between 200 and 700 nm, from the near ultraviolet to visible red. Thermo-sensitive hydrogel volume changes may be induced by radiation up to 2000 nm. Ionizing wavelengths are shorter than 125 nm, and are not used. An embodiment incorporates sulfonate-based water-soluble photoswitches that induce volumetric hydrogel expansion upon exposure to nonionizing radiation, and contract under darkness, in a reversable process. Modifying pH and the critical solution temperature of constituent polymers during hydrogel preparation allows expansion and contraction parameters to be explicitly tuned. In an embodiment, the nonionizing radiation is a blue light with a wavelength 405 nm, which causes spiropyran and merocyanine to interconvert, given the hydrogel has acrylic acid merocyanine incorporated. Under light irradiation, the acidic internal gel environment quickly and completely converts the hydrophilic merocyanine to the hydrophobic spiropyran, allowing rapid swelling of the gel from a first to a second condition in less than 90 seconds. Another embodiment prepares the hydrogel by dissolving spiropyran monoacrylate in dimethyl sulfoxide to form a water-soluble photoswitch. This also has volumetric expansion on exposure to photons, and contraction under dark conditions. In a related embodiment, light can be used to reversibly control the association between a photoswitchable azobenzene guest and an α-cyclodextrin host. This supramolecular cross-link interaction causes reversible expansion and contraction of the hydrogel when irradiated.

An embodiment uses photochromic compounds and photochromic moieties other than azobenzenes and spiropyrans to incorporate in the media, such as diarylethenes, spirooxazines and thiospiropyrans, sulfonated spiropyrans, fulgides, diarylethenes, stilbenes, bisimidazols, spirodihydro-indolizines, quinines, fulgide, dithienylethene, hydrazines, anils, thiosulfonates, hexaarylbiimidazoles, azotolene, imines, coumarins, and nitrobenzyls, and similar substances as these, their moieties, derivatives of these, and mixtures thereof. The photochromic materials are selected depending on their compatibility with the polymer matrix, their activation and response rates, and other conditions required of the gel-like media. Peptide crosslinkers containing enzymatically degradable groups and a photoreactive group can form useful chemical patterns. The stiffness and stretchiness of embodiments can be modifying with different monomer lengths and concentrations in the network, and also by changing the concentration of linkers in the prepolymer solution.

In another embodiment, the gel-like media used to control capsule motion include liquid crystal polymers. In an embodiment, nonionizing radiation causes surface strains in three-dimensional liquid crystal polymers, reshaping them. Crosslinked liquid crystalline polymers create alignment layers and alignment structures when exposed to light. These structures, composed of rigid and flexible parts, align mesogen moieties in one direction to form rod or disk shapes. They can be transformed between a nematic phase, the most fluid liquid crystalline state, and smectic or columnar phases, both more ordered and less fluid, forming rod and disk shapes, respectively.

In an embodiment, liquid crystal polymeric materials are made sensitive to light through photochromic groups incorporated as molecular switches in the polymer structures. Their incorporation can form materials with macroscopic spring-like properties. In an embodiment, light induces expansion, bending, and helical shapes. The mechanism of shape transformation may be based on selective absorption of light of a specific direction. Photochromic moieties in side chains along polymer backbones can act as both mesogens and photoresponsive groups. Because they can form distinct shapes, an embodiment can use liquid crystal polymeric materials to decelerate and/or stop a controlled motion capsule, without a large change of their absolute volume.

In an embodiment, the container is configured so that the reversibly swelling and shrinking gel-like media is sealed with an external membrane layer which expands and contracts with the gel-like media. The membrane layer may be a surface that is non-degradable and is selected for its porosity permeability. Suitable materials for the membrane layer include, but are not limited to, different polymers and copolymers, silicone, elastomers, resins, polyurethanes, and other materials. Membrane layer integrity and permeability are important values. In an embodiment, permeability is desired, to transfer tubular structure moisture in the process of the gel-like media's swelling, and expel moisture in the process of the gel-media's shrinking. Membrane layer vapor permeability moisture transfer is a superposition of phase transfer over the membrane's porous space, and diffusion over the polymeric matrix volume. Starting from an initial time, water vapor enters a membrane through capillaries, and is adsorbed on pore walls and wall material, at an established rate for a given membrane material. Only when a constant moisture gradient is established over the membrane's cross-section does water vapor transfer to the material within the membrane. This is a critical period, because a gel-like media's macroscopic, physical response to radiation depends on the length of time before water vapor transfers to the media. Using the Zolotarev-Dubininin model, the time prior to gel-like media swelling can be determined as a function of ratio between the membrane and polymer pore space diffusion coefficients, measured membrane porosity and solubility or sorption capacity, as well as membrane layer thickness and temperature, all which impact the rate of gel-like media absorption, and hence swelling.

An embodiment will use membranes with moisture vapor transmission rate [MVTR] between $$\sim 100\text{--}\sim 20{,}000 \text{ g}\cdot\text{m}^{-2}\cdot\text{d}^{-1}$$

Vendors often use $\text{g}\cdot 100\text{-in}^{-2}\cdot\text{d}^{-1}$ to define membrane layer MVTR, such that:

$$100 \text{ g}\cdot\text{m}^{-2}\cdot\text{d}^{-1} = 7 \text{ g}\cdot 100\text{-in}^{-2}\cdot\text{d}^{-1}, \text{ and } 20{,}000 \text{ g}\cdot\text{m}^{-2}\cdot\text{d}^{-1} = 1{,}400 \text{ g}\cdot 100\text{-in}^{-2}\cdot\text{d}^{-1}.$$

Some materials for membrane layers include, but are not limited to, polyurethane elastomers, which have high permeability towards water vapor and are biocompatible; fluoropolymers, silicone, resins, high molecular weight polyethylenes, cellulose nanomaterials, carboxymethyl cellulose materials, polylactic acid films, polyhodroxybutyrate films, and other thermoplastics, biopolymers, and elastomers. An embodiment uses thin or ultra-thin membrane layers, the vapor flux controlled with skin MVTR and thickness. In an embodiment the membrane layer maintains a constant relative pore size during expansion.

In an embodiment the membrane layer has an interpenetrating delamination-resistant bond with the gel-like media, such as an elastomer skin interlocked to a hydrogel filling. The elastomer skin provides some barrier against excess hydrogel water loss. An interlocked elastomer, such as a silicone elastomer, can be sufficiently elastic to expand when the hydrogel swells, and contract when the hydrogel shrinks. In an embodiment the gel-like media is a multifunctional material that combines mechanical robustness with swelling capacity in which a distinct membrane layer is not necessary or used.

In an embodiment the gel-like media has a selective self-healing function that responds to pressure exceeding a threshold or the sundering of a continuous part. A self-healing embodiment integrates graphene with polymers to promote gel-like media self-healing after excessive bending or stretching, such as what may happen in an intestine, when the swollen gel-like media is impacted by fluid, sediment, and epithelial forces. Another self-healing embodiment may use polymers with reversible crosslinks based on acryloyl-6-aminocaproic acid, characterized by large swelling capacity and an ability to regenerate. They are obtained by uncomplicated synthesis. In these hydrogels the self-healing property may be induced by strong van der Waals interactions that connect separate pieces of a sundered gel-like media. In another self-healing embodiment hydrogels are modified with nanoparticles and/or microparticles to reduce swelling and promote self-healing. Microparticles or nanoparticles dispersed in the polymer matrix polymerize a complex with a ruptured polymer.

In an embodiment, microparticle or nanoparticle incorporation can concentrate in the surface of the hydrogel, forming an inherent barrier to porosity and structural damage. No membrane layer may be needed. In a fail-safe embodiment, microparticle and nanoparticle incorporation in the shape changing material can be activated to break down the shape changing material, triggered by detection of conditions in which the shape changing material poses a medical risk. Hydrogels containing cells that contain amino acid sequences that be degraded by plasmin or matrix metalloproteinases cleave the hydrogel if activated by a nonionizing radiation of a different wavelength than the wavelength used to swell the hydrogel. In another fail-safe embodiment a recombinant protein is crosslinked in a hydrogel, making the hydrogel capable of being decomposed if the controlled motion capsule releases a specific enzyme. In another fail-safe embodiment nonionizing radiation of near ultraviolet and visible light swells the hydrogel, while nonionizing radiation between about 250-350 nm cleaves polymer bonds, particularly high molecular weight polymer chains, causing the shape changing material to liquefy. These and other embodiments are fail-safe because the shape changing material breaks down if it poses a risk.

An embodiment includes gel-like media comprising liquid crystal elastomers, instead of, or along with, hydrogels. Liquid crystal elastomers are highly elastic, but can be 'programmed' to have little or no water vapor exchange. In a liquid crystal elastomer embodiment no membrane layer may be needed. In general, an embodiment in which a gel-like media has a surface of restricted permeability may not require a membrane, if such a surface has sufficient robustness and resilience to protect and preserve the media, and expansion occurs without moisture transfer.

The gel-like media, composed with an independent membrane layer, or not so composed, forms a shape-changing material. This may be a material with relatively static shape that is forced into a different configuration by a stimuli, or a material with a dynamically changing shape under certain conditions and/or stimuli.

An embodiment may include membrane layers that are coated with various materials to introduce desired characteristics, which may be formed from one piece or from multiple pieces. The combination of membrane materials, coatings, and arrangement of pieces modulate the membrane layer's surface energy, which cause it to expand in a certain shape. The gel-like media swelling causes the membrane layer to expand in a shape as it stretches, which thereby constrains the gel-like media shape. Such shapes may include, but are not limited to, helical, pyramidal, conical, rectangular, oblong, elliptical, or other shapes. It is advantageous that the shape-changing material on each side of the container swell to an extent of 5 mm, 10 mm or 15 mm, or more, to decelerate and stop the controlled motion capsule motion.

At least one nonionizing radiation emitter is disposed in close proximity to the gel-like media in the container. In an embodiment the emitters are in the form of at least one light source next to the top, and at least one light source next to the bottom, of the container, and able to continuously irradiate the gel-like media as it swells and shrinks. A transparent surface may be disposed between each light source and the container, to permit radiation to pass unattenuated. In a further embodiment emitters are located within the container. In an embodiment, when the gel-like media swells it causes emitters to move and remain in optimal communication with the gel-like media. When emitters reduce or cease radiation, the gel-like media shrinks and emitters remain positioned within the gel-like media. Emitters are moved in the direction of the shape-changing material motion.

In another embodiment the emitters are extended along the sides of the container, flooding the container cavity with nonionizing radiation when activated. In an embodiment emitter radiation is projected out of the container, in the direction of the gel-like media swelling motion. This embodiment of the emitters may also be used with thermosensitive shape-changing materials, in which the nonionizing radiation causes a temperature change in the gel-like media.

An implementation of the controlled motion capsule may include data from at least one sensor on or close to the surface of the controlled motion capsule body, a positioning program module that processes the sensor data, and a controller that activates and deactivates the nonionizing emitters proximate to the reversibly swelling and shrinking gel-like media; data from the at least one sensor is used by the positioning program to calculate the velocity, deceleration, acceleration, slew, turns, and cessation of movement of the controlled motion capsule, incrementally and by time segments; the results of this calculation identify a trajectory and locate the controlled motion capsule's somalocation. The somalocation may be used by the controller to determine at least one value which is used to execute an intensity and/or duration of emitter activity. The device also includes a power source for providing power to emitters.

In accordance with an embodiment, the controlled motion capsule includes at least one controller that monitors the data, such as data of a dynamic parameter from the interior of a body tubular structure, and determines at least one value, such as a set of values for each data monitored, the controller is coupled to at least one nonionizing radiation emitter and is configured to execute programmed instructions stored in memory including determining the intensity and/or duration of energy activating the at least one nonionizing radiation emitter for the set of values determined by the data, the controller further determining a change in the intensity and/or duration of energy activation due to feedback about the dynamic condition of the shape changing materials, the controlled motion capsule somalocation, and/or the local body tubular system.

In an embodiment the controller may use a feedback system in the positioning program. Feedback may include data from at least one or more of the following nine inputs. 1) The membranes covering the gel-like media are connected to the controlled motion capsule and may transmit membrane expansion rates and frictional data to the controller. 2) Camera systems may provide data that can be used to compare an optical flow field with a background (predetermined or computed) optical flow field, and thereby estimate the speed of the camera motion. 3) Camera systems may provide data that can be used to compare an optical field pattern with a background (predetermined or computed) optical field pattern, and thereby estimate the body tubular environment and location. In an embodiment using optical flow fields and/or optical field patterns, an adaptive threshold may be used to avoid false positives in visual measurements. 4) Single and multiple axis accelerometers may be used to detect the magnitude and the direction of acceleration/deceleration, as well as orientation, vibration, and shock data. Micromachined microelectromechanical systems (MEMS) accelerometers may be preferred. 5) Miniaturized magnetometers may be used to determine absolute direction of motion. 6) MEMS gyroscopes may be used to detect and measure the rotation rate and pose of the controlled motion capsule. 7) One or more sensors may used, such as a motion sensor that detects movement data of the controlled motion capsule. Sensors may include sensing materials with stimuli response (light, humidity, mechanics, etc.) and multiple detection features. 8) Environmental gauges may be used, to assess the temperature, pH, electrostatic charge, and/or moisture level data within the tubular structure surrounding the capsule. 9) Spectral and hyperspectral imaging may be used to detect microbial population distribution and volume data.

The controller may include a timing system to process the controlled motion capsule's position and orientation in the body tubular structure, such as the GI tract. The controlled motion capsule may operate automatically, the device activating the reversibly swelling and shrinking media according to programmed instructions. As previously stated, precise position and duration of presence are key factors in the controlled motion capsule's success. The device can include a transceiver to send data to, and receive input from, an external resource, such as a human operator or a processor, and this external resource may activate the nonionizing radiation, thereby causing a response in the reversibly shape-changing material. The human operator or the external processor may use observation methods that include, but are not limited to, the methods of ultrasound, x-rays, and/or another sensing or viewing system.

In an embodiment, the controlled motion capsule sensors may detect when conditions of the tubular structure, such as the GI tract, deviate outside of predetermined ranges or conditions, such as pH, temperature, size, and/or microbial populations. In response the controller can activate the reversibly shape-changing material to decelerate and/or stop the controlled motion capsule. In an embodiment a wireless communicator can notify an external agent of the conditions detected, and the position, velocity, and status of the controlled motion capsule. Under predetermined parameters, the controlled motion capsule can remain in a certain location until it receives a signal, although a fail-safe system prevents this from causing intestinal blockage. In an embodiment the controlled motion capsule has recording systems on-board to record visual, chemical, electrophysiological, and/or other data of the environment the controlled motion capsule is located in. In an embodiment these recording systems are automatically configured to operate under specific conditions, such as when the controlled motion capsule decelerates and/or stops movement in response to the detection of conditions outside predetermined ranges or conditions. In an embodiment the recording systems are configured to operate when the controlled motion capsule decelerates and/or stops movement at certain locations in the tubular structure, such as GI tract. Other methods of triggering the recording systems include an external agent's input, or via a periodic or stochastic activation function. In an embodiment the controlled motion capsule releases therapeutic compounds in response to sensor data of predetermined conditions, specific locations, and/or input from external agents. The reaction of the environment around the controlled motion capsule to the therapeutic compound release can be monitored and recorded. In this way, therapy impact can be precisely monitored while the controlled motion capsule has ceased movement.

In an embodiment, the controlled motion capsule may stop in a position where it does not cause intestinal blockage. In this position the controlled motion capsule can provide therapeutic treatment over an extended time frame. The advantage of controlling capsule movement is that the capsule can be used at specific times. For example, it can provide stimulation that induces intestinal secretions and/or provide stimuli that increase or decrease microbial activity. It can do so at times that correlate with circadian rhythms, which is important in some disease treatments.

Further details of these and other embodiments and aspects of the invention are described more fully below with reference to the accompanying figures.

BRIEF DESCRIPTION OF THE FIGURES

The present invention will be understood and appreciated more fully from the following detailed description taken in conjunction with the drawings in which.

DETAILED DESCRIPTION

Figure 1:
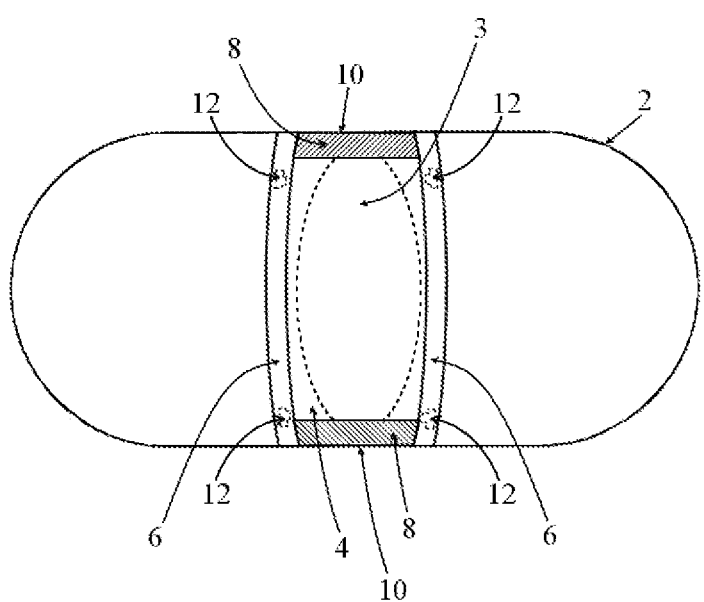
FIG. 1 is a schematic illustration of a gel-like media housed in a container of a controlled motion capsule.

As illustrated in FIG. 1, an embodiment of controlled motion capsule 2 may include a gel-like media 3 configured to fit within a container 4, defined by structural elements 6. The container 4 may include an expandable and contracting membrane layer 8 configured to seal the swelling gel-like media 2 and covering all openings 10 of the container 4. Controlled motion capsule 2 may also include nonionizing radiation emitters 12 capable of activating the gel-like media 3 which may respond by reversibly swelling, causing membrane layer 8 to reversibly expand, thereby always protecting the gel-like media 3 in the membrane layer 8 interior.

Figure 2:
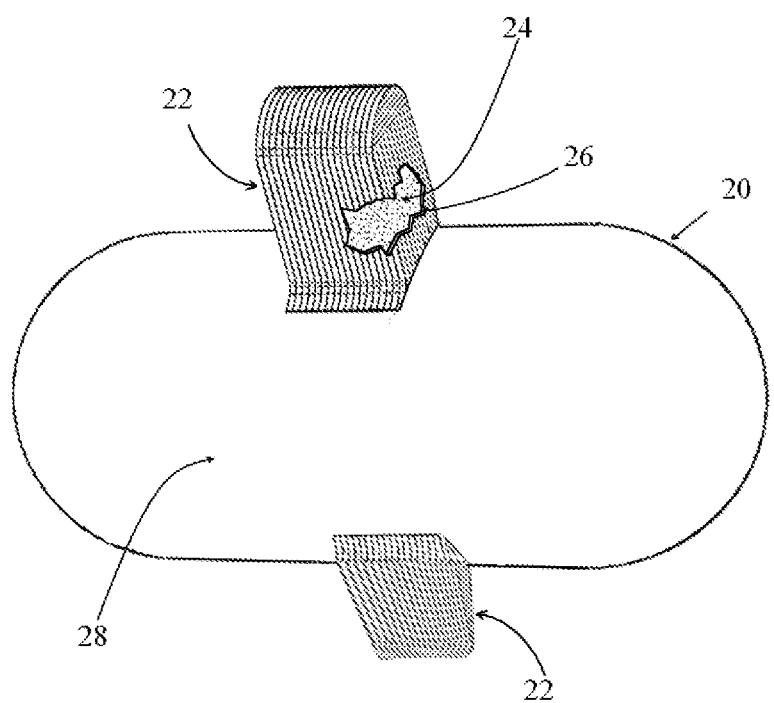
FIG. 2 is an isometric illustration of membrane-covered gel-like media in an expanded and swollen condition.

FIG. 2 illustrates a possible configuration of the controlled motion capsule 2, in which a membrane layer 22 has expanded, due to a gel-like media 24 within it which has swelled, the gel-like media 24 being sealed underneath the membrane, therefore the gel-like media 24 is only visible through the cut-away 26 in membrane layer 22. Controlled motion capsule's surface 28 materials may include polymers, woven and nonwoven components, and composites, that are biocompatible and physically robust for the use environment.

Figure 3:
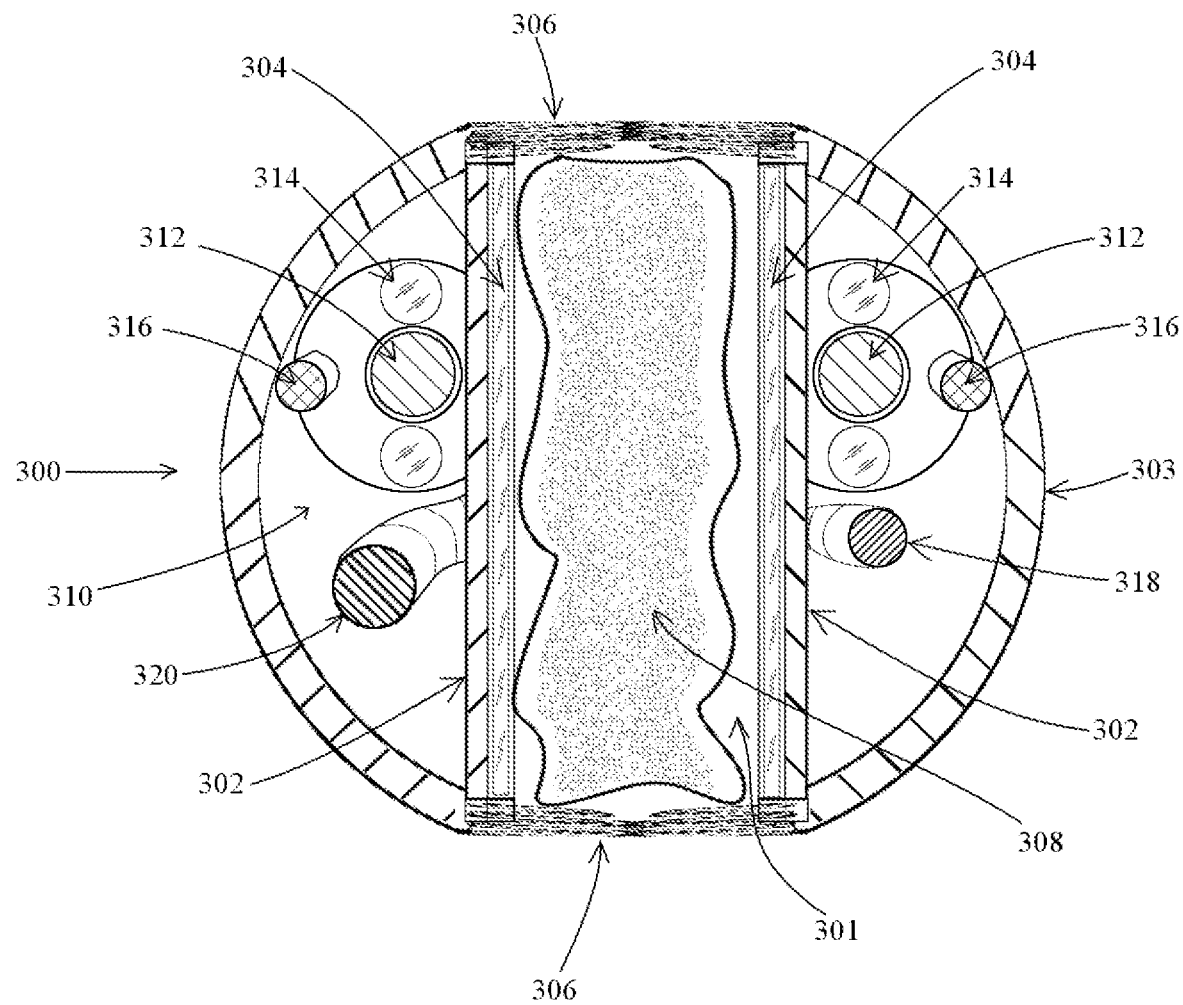
FIG. 3 is a cross-sectional view of an embodiment of a controlled motion capsule including the container with gel-like media within.

FIG. 3 is a cross sectional view of the controlled motion capsule 300, defined in cross-section by capsule wall 303, and including, in cross-section, a container 301, defined by container walls 302, the inner part of which includes a transparent section configured with nonionizing radiation emitters 304, which are bar emitters with emissions that penetrate much of the surface of gel-like media 308. Container 301 is covered by membrane layers 306, which function to seal gel-like media 308 in container 301, and membrane layers 306 function to expand when gel-like media 308 swells. The inner surface 310 of one end of the controlled motion capsule includes recording devices (cameras) 312 to detect and record the external environment, and illuminators 314 that shine on the external environment. Recording transmission cables 316 serve to transmit detections to another part of the controlled motion capsule 2. Signal cable 318 functions to transmit operational data and instructions. Power cable 320 transmits energy to operate the nonionizing radiation emitters 304, recording devices 312, and illuminators 314, among other things.

Figure 4:
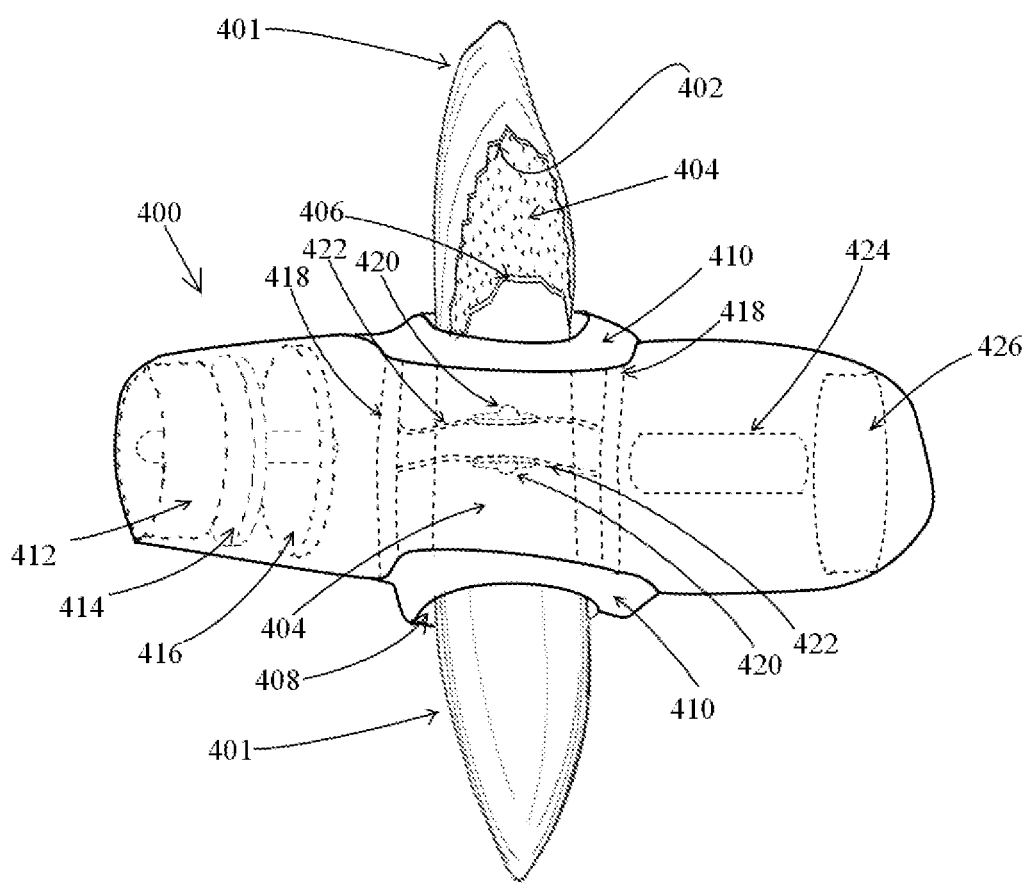
FIG. 4 is a pictoral and schematic illustration of an embodiment of a controlled motion capsule including the membrane-covered gel-like media in an expanded and swollen condition.

Referring now to FIG. 4, shape-changing materials 401 are shown in an expanded position. In this position, the membrane layers 402 have been expanded by the force of the gel-like media 404 swelling, sealed in membrane layers 402 and visible in cut-away 406. Membrane layers 402 are constructed, and attached to the container 408, which is within protected openings 410, such that shape-changing materials 401 have an expanded shape that extends in a length perpendicular to the controlled motion capsule 400 longitudinal shape. The gel-like media 404 and membrane layers 402 form the shape-changing materials 401 with a thickness, length, and resilience, that may displace fluids, suspended solids, and when pressed against tissue, cause the tissue to displace.

A variety of elements may be housed within controlled motion capsule 400, depending on the preferred purpose it is used for. Some of the elements may include, illustrated with broken lines because they are inside the controlled motion capsule 400, a camera 412, a controller 414, a CMOS sensor 416, the container 408 defined by container walls 418, nonionizing radiation emitters 420 supported by cables 422, positioned within the gel-like media 404. This embodiment includes a power source 424 and a communication transducer with an antenna 426. Those skilled in the art will understand and appreciate that different elements known in the art can be used, depending on the different inspection and/or treatment purposes the device is used for, as well as the particular body tubular structural dimensions and qualities the device is used in.

Figure 5:
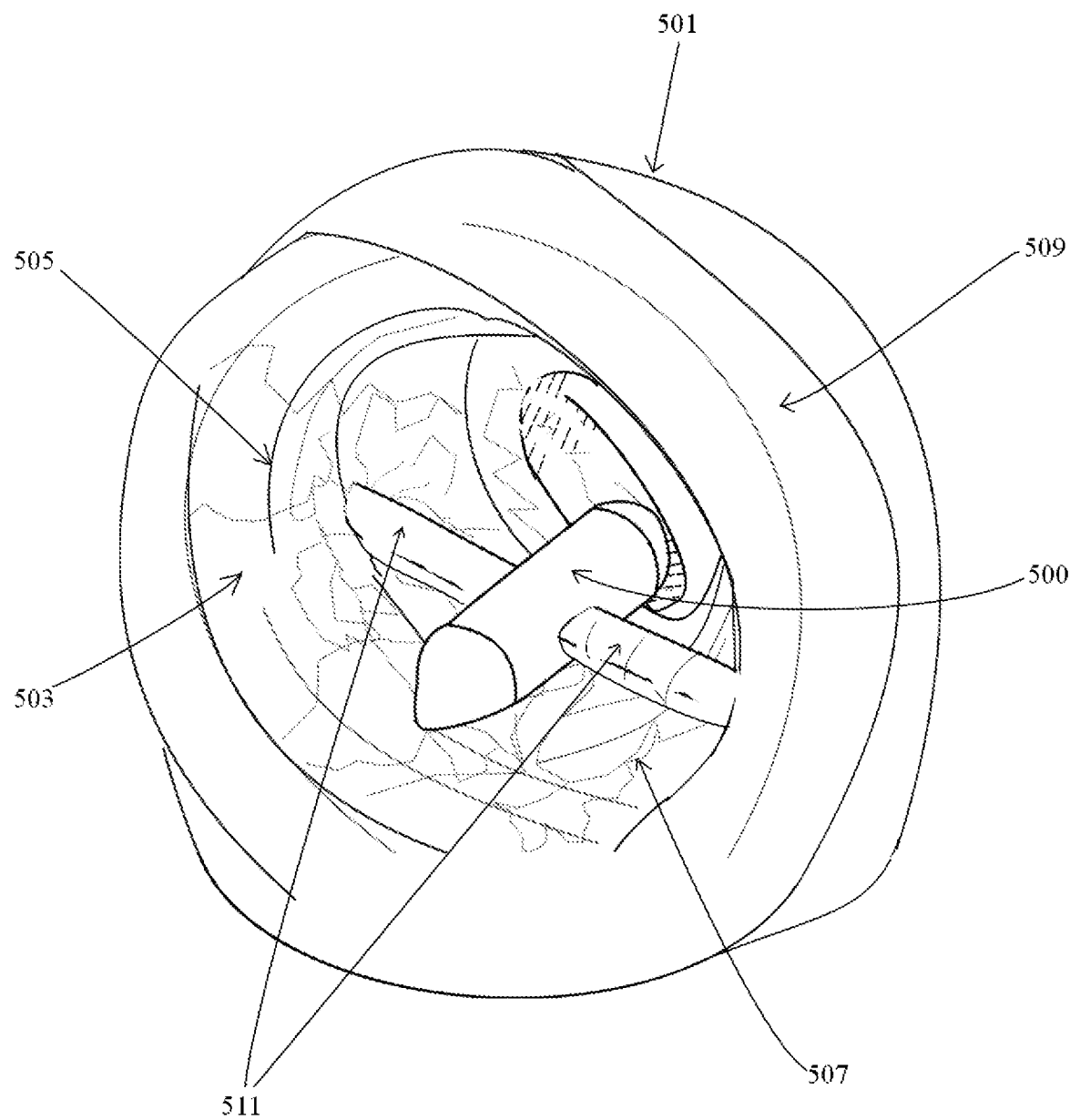
FIG. 5 illustrates an example of the operation of a controlled motion capsule within a body tubular structure.

FIG. 5 depicts a controlled motion capsule 500 in a body tubular structure, in this case a gastrointestinal structure 501, within which is an epithelium surface 503 with plicae circulares ridges 505 and lamina proproria edges 507, the outside of the wall showing the serosa 509. The expanded shape-changing materials 511 are assembled to direct expansion perpendicular to the elongated dimension of the controlled motion capsule 500, thereby interfering with peristaltic flow, which decelerates the controlled motion capsule. In a preferred embodiment the shape-changing materials 511 are configured to reach the tubular structure wall's epithelium surface 503, and gently press against it. Shape-changing materials 511 press into the plicae circulares 505 and lamina propria 507 and the epithelium surface 503 generally, sufficiently to arrest forward motion. Because the shape-changing materials 511 are soft, tissue-like materials, they do not damage the microscopic villi that cover the plicae circulares.

Figure 6:
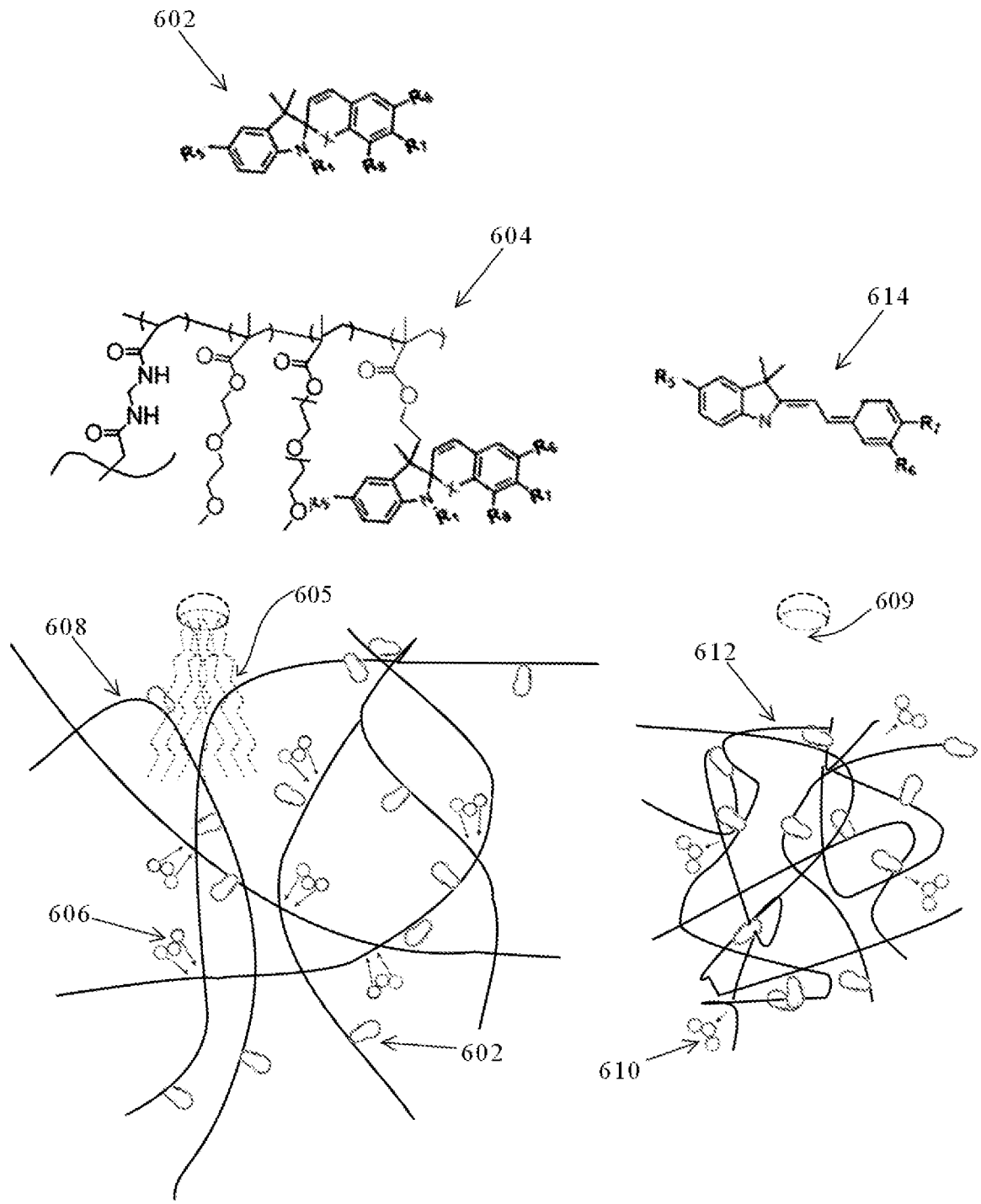
FIG. 6 is a schematic illustration of a sulfonated spiropyran hydrogel system in a gel-like media.

FIG. 6 illustrates an embodiment in which the gel-like media is a hydrogel synthesized from polymerizable sulfonated spiropyran molecules 602 covalently incorporated into cross-linked polymer networks 604, defined by low critical solution temperature polymers, such as oligo (ethylene glycol) methyl ether methacrylatec, as well as initiators. When exposed to nonionizing radiation 605, the sulfonated spiropyran charge density increases, causing water 606 to diffuse into the polymeric network and expanding polymer chains 608, interspersed with the sulfonated spiropyran molecules 602. When nonionizing radiation ceases 609, spiropyran charge density decreases, water diffuses out 610 of the gel and collapses polymer chains 612, and spiropyran isomerizes to the merocyanine form 614.

Figure 7:
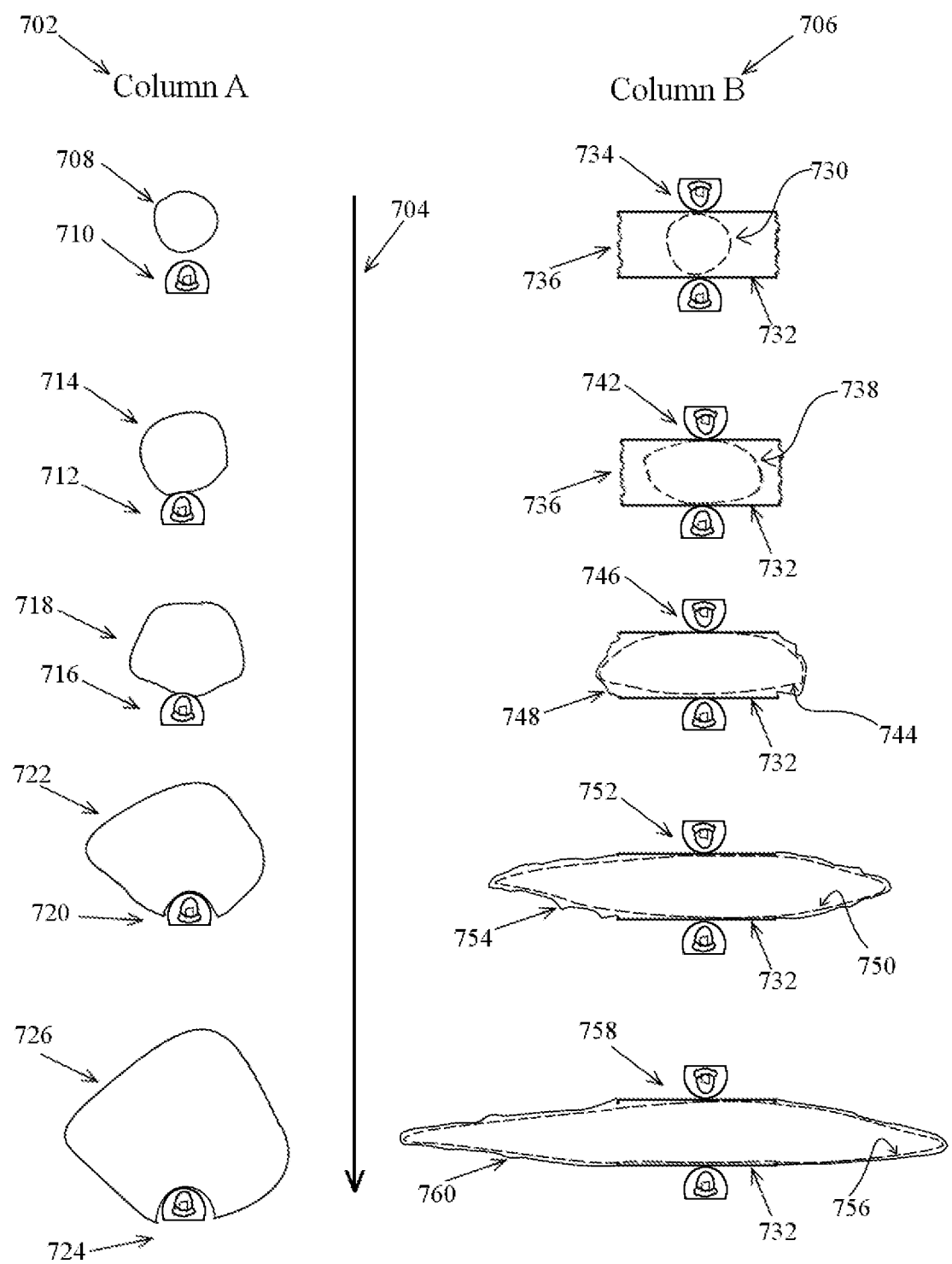
FIG. 7 illustrates unconstrained swelling of the gel-like media and swelling constrained by the present invention's components.

FIG. 7 illustrates an aspect of an embodiment to show its progression during a transformation. The aspect concerns a reversible shape-changing hydrogel comprising a photoreactive group configured to undergo a reversible photochromic reaction in response to nonionizing radiation. In Column A 702, the hydrogel swelling is displayed in response to the time and/or intensity of nonionizing radiation. The arrow 704 is pointed towards increasing radiation time and/or intensity. In Column B 706, the hydrogel swelling is constrained by the controlled motion capsule container and the membrane layer that surrounds the hydrogel.

Hydrogel 708 is in an initial state in which the hydrogel matrix is only hydrated with primary bound water. Emitter 710 is de-energized. Emitter 712 is activated. Hydrogel 714 interacts with hydrophobic groups and gains secondary bound water. Emitter 716 continues and may intensify activation. Hydrogel 718 has matrix osmotic force driven towards dilution which is resisted by crosslinks, causing more water absorption. Emitter 720 continues and may intensify activation. Hydrogel 722 absorbs more water as the nonionizing radiation interacts with polymer chains. Emitter 724 continues and may intensify activation. In hydrogel 726 the network and crosslinks hold the fluid and an elastic force is completed by the full expansion of the hydrogel.

Hydrogel 730 is in an equivalent state to hydrogel 708, but is in container 732, which has de-energized emitters 734 on two sides. Membranes 736 cover two ends of container 732. Hydrogel 738 is in an equivalent state to hydrogel 714, but is in container 732, which has emitters 742 that are in an equivalent state to emitter 712. Hydrogel 744 is in an equivalent state to hydrogel 718, but is in container 732, which has emitters 746 that are in an equivalent state to emitter 716. Membranes 748 expand as hydrogel 744 swells.

Hydrogel 750 is in an equivalent state to hydrogel 722, but is in container 732, with emitters 752 that are in an equivalent state to emitter 720. Membranes 754 expand as hydrogel 750 swells. Hydrogel 756 is in an equivalent state to hydrogel 726, but is in container 732, with emitters 758 that are in an equivalent state to emitter 724. Membranes 760 expand as hydrogel 756 swells.

Figure 8:
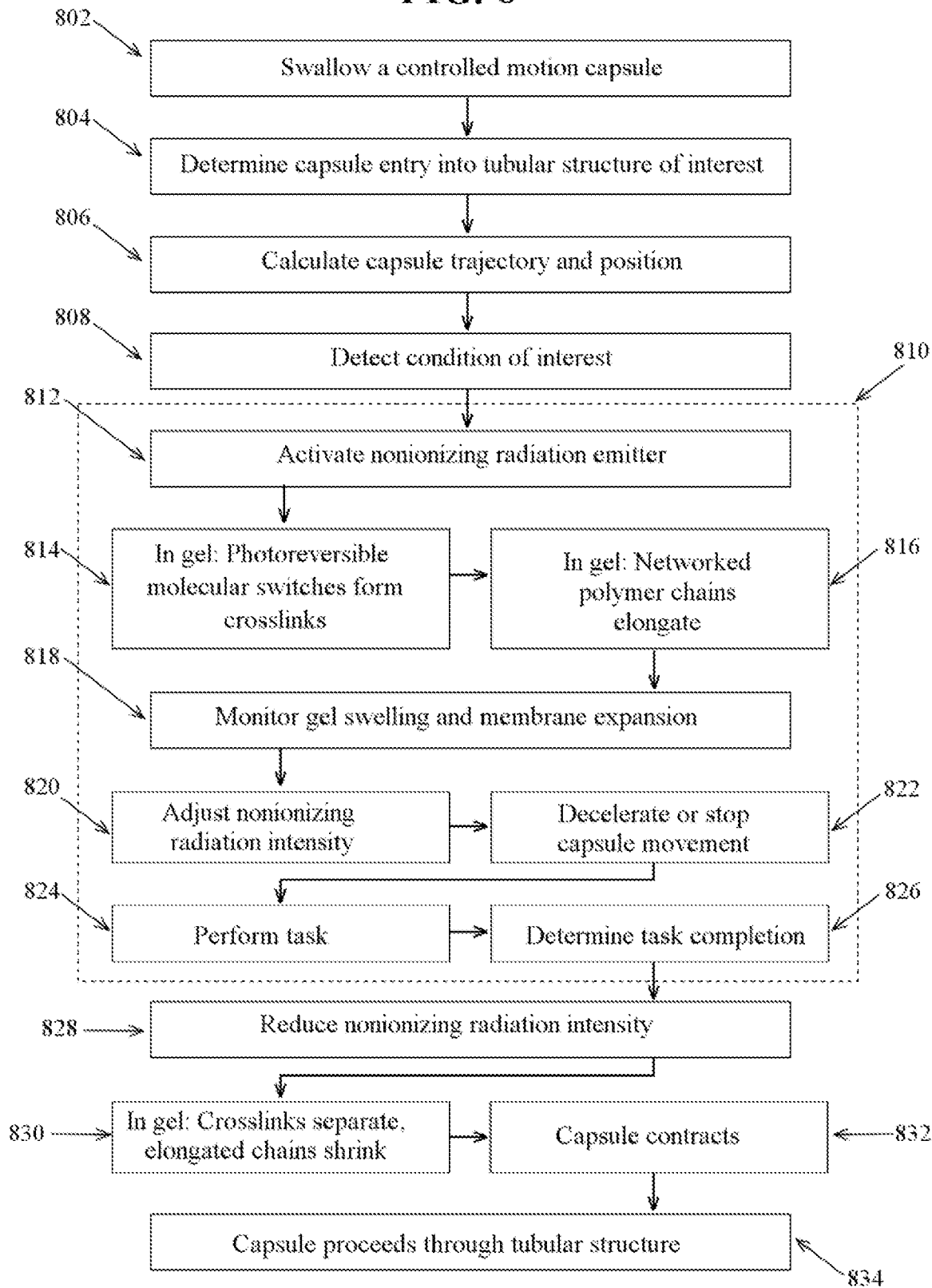
FIG. 8 is a flow diagram of a method of the using the controlled motion capsule.

Reference is now made to FIG. 8 which illustrates, in flow diagram format, a method of using a controlled motion capsule, in accordance with preferred embodiments of the present invention. The process begins with swallowing the capsule 802. After passing through parts of the digestive system, the capsule enters the tubular structure of interest 804, which may be the small intestines, or specifically the Doudenum, the Jejuneum, the Ileum, or another component. Elements in the capsule calculate its trajectory and position 806. They detect a condition of interest 808, such as a region outside of ordinary threshold measurements, a distinct color pattern, or some other factor. The capsule then enters its deceleration phase, which is marked by dotted line 810. The nonionizing radiation emitter is activated 812, which induces the gel-like media to form crosslinks from photoreversible molecular switches 814, which leads to the gel-like media's networked polymer chains elongating 816. As this causes the gel-like media to swell, the capsule monitors the swelling and associated membrane expansions 818. The capsule's controller adjusts the nonionizing radiation intensity and/or duration 820 accordingly, in order to decelerate or stop the capsule movement 822. This permits the capsule to perform a task 824, such as a medical task to inspect, treat, or sample something. The capsule's controller determines when the task is complete 826. Once completed, the deceleration phase ends, and nonionizing radiation intensity and/or duration are reduced, including reduced to zero 828. This causes the crosslinks in the gel-like media to separate, and the elongated chains shrink 830, leading the gel-like media to shrink, and the overall dimension of the capsule to contract 832. In this smaller form, the capsule continues through the area it is in 834 without impediment.

Figure 9:
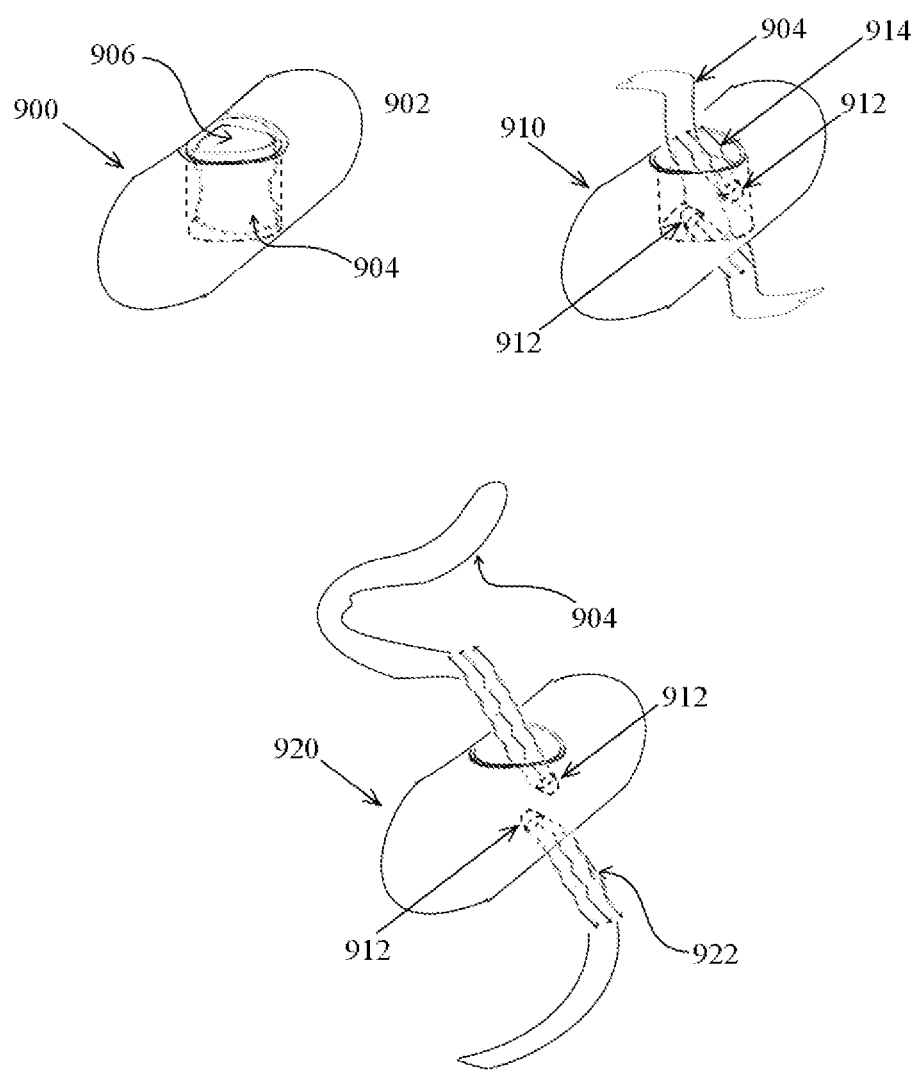
FIG. 9 shows a series of aspects of the controlled motion capsule wherein the shape changing material is a stimuli-responsive polymer.

FIG. 9 shows a controlled motion capsule 900 in which the container 902 stores a polymer-based shape changing material 904 that exists in different phases. Shape changing material 904 remains in container 902 unless exposed to certain stimuli, such as light of certain wavelengths. The surfaces of shape changing material 904 that are exposed to external environments, such as 906, do not respond to stimuli, therefore the device remains in compact form in ordinary use circumstances. In controlled motion capsule 910, energizing emitters 912 activate, and expose shape changing material 904. Shape changing material 904 develops a different molecular internal order, shaped by alignments. The emitters 912 radiate 914 inside and out of the container 902, thereby continuing to modify shape changing material 904 as it changes form.

Controlled motion capsule 920 shows shape changing material 904 deformed in the arrangement direction. Energizing emitters 912 continue to activate shape changing material 904, by the duration and intensity of their radiation 922. In an embodiment the emitters 912 radiation 922 intensifies as shape changing material 904 is further deformed.

Because the shape changing material may press against epithelial walls of a body tubular system, it is beneficial there to be included in the material, or the material's surface layer, including a membrane layer, a component significantly improving adhesion resistance, such that the component blend is beneficial for the shape changing material to resist adhesion and material distortion during contact with body tubular systems.

While the invention places principal reliance on the reversible polymer system to provide the fail/safe condition required for safe use of the device, in some cases the expanded shape changing material may require detachment from a controlled motion capsule to permit the controlled motion capsule to be transported safely through a body. In some cases it may further be necessary that the shape changing material dissolve, because of detected conditions that may include, but are not limited to, the shape changing material impeding desired motion of the controlled motion capsule, or because a period of time has elapsed.

It is desirable that the shape changing material exhibit a plasticity that is selected for particular medical and commercial processes.

Embodiments may be configured for other organisms than humans, and for tubular structures in the body besides the GI tract, including the urinary tract, the abdominal cavity, the chest cavity, the female or male reproductive tracts, cranial and spinal subarachnid spaces, middle ear tubes, as well as artificial tubes used in medicine. The embodiments herein include tubular spaces in which fluid flows. Fluids include liquid, gas, or mixtures thereof that also may have solid particles therein. Unicellular, fungal, and aggregated cell systems may be present in fluid. Some examples include digestive fluids, intestinal material, bile, mucous, saliva, urine, serum, or blood. Modifications of the controlled motion capsule may be made, such as in its dimensions, structural materials, gel-like media composition, nonionizing radiation source and range, and membrane flexibility, porosity, and design, to properly suit the device for the purpose of use.

As used herein, the terms "swelling" and "expanding" when describing the gel-like media and membranes of the embodiments of the present invention refer to a change in size of gel-like media and membrane layers from an initial size to a size larger than the initial size by any continuous amount up to about two times to at least five times. "Swelling" is used to indicate an association or absorption of water, water vapor, external moisture, or of water and an organic compound useful in the practice of the invention. The change in size can be accompanied by a change in shape, or the shape may remain substantially the same with the increase in size. Although the terms "swelling" and "expanding" may be used incherchangeably herein, the term "swelling" is used generally to refer to the gel-like media, and the the term "expanding" used generally to refer to the membrane layers and the shape-changing material. The term "expanding" need not be associated with water transport.

As used herein, the terms "shrinking" and "contracting" when describing the gel-like media and membrane layers of the embodiments of the present invention refer to a reduction in size of the gel-like media and membrane structures to a size smaller than the size when the structures have been swollen and expanded. The change in size can be accompanied by a change in shape, or the shape may remain substantially the same with the decrease in size. The terms "shrinking" and "contracting" may be used incherchangeably herein, with the term "shrinking" being used generally to refer to the gel-like media, and the the term "contracting" used generally to refer to the membrane layers and the shape-changing materials. The gel-like media, membrane layers, and shape-changing materials may be reduced in size to the same or substantially the same size as their initial state prior to activation. They may only be reduced in size to an extent that allows smooth passage through the GI tract. In exemplary embodiments the shape-changing materials contract to within the capsule.

The term "membrane layer" refers to a surface anterior to the gel-like media which expands and contracts as the gel-like media swells and shrinks, such that the membrane layer remains in contact with the gel-like media, to operatively permit liquid absorption and desorption in the gel-like media, and protect the gel-like media from damage. A membrane layer may form as skin on the gel-like media, and interlock such that it does not delaminate.

The term "shape-changing material" refers to a material with relatively static shape that is forced into a different configuration by a stimuli, or a material with a dynamically changing shape under certain conditions and/or stimuli. It includes liquid crystal elastomers that modify shape but not volume, and hydrogels that primarily modify volume. It includes membrane layers if they are present.

As used herein, a "fail-safe" system refers to any condition in which, should the device not operate for any reason, the shape changing materials, gel-like media and membranes remain in their initial, shrunken and contracted state in the capsule, or the shape changing materials, gel-like media and membranes shrink and contract to their initial states or sufficiently reduce in size to an extent that allows smooth passage of the device through all the tubular structures to allow it to safely exit the body.

As used herein, "somalocation" is defined as a location inside a body, identified by means of analog or digital information. It may be a location relative to an external coordinate system, equivalent to an inside-of-the-body geolocation; a location relative to an inside-of-the-body coordinate system; a location relative to a distance on an internal body map; a location relative to biological and/or abiotic attributes or conditions inside of a body; or a location relative to a conditional, unique, or conceptual coordinate space as may arise in practice.

A "stimuli" is defined herein as a nonionizing wavelength energy used by a material to change shape.

"Nonionizing radiation" is defined herein as near ultraviolet, visible, and near infrared light, wavelengths between 200 nanometers and 2,000 nanometers. These light wavelengths can be safely produced by low-power emitters such as LEDs at various intensity levels, resulting in the desired degree of the shape changing material expansion and gel-like media swelling.

"Variably energizes", "variably energizing", "variably de-energizes", "variably de-energizing", "variably activating" and "variably deactivating" are defined herein as any level of energy activation of a system, including complete lack of energizing, de-energizing completely or to some intermediate degree, energizing completely or to some intermediate degree, energizing and de-energizing a system for a specific time-frame, doing so at any level of energizing, and periodic or inconsistent energizing and de-energizing.

"Variably decelerated" is defined herein as any velocity change, from no deceleration to complete deceleration (stoppage.) "Variably accelerated" is defined as any velocity change.

"Variably inflated" and "variably deflated" are defined herein as any degree of volume change from an initial volume to a greater or lesser volume.

A "signal" is information encoded in formats that, should it pass a threshold of minimum intensity, may cause an activity to occur.

A "catalyst" reduces the activation energy required to initiate a change in a material.

A "hydrogel" is a hydrophilic three-dimensional (3D) network that is chemically crosslinked or physically entangled with excellent water swelling capacity.

"Gel-like media" is defined herein as any soft material that mimics some of the biochemical and biophysical properties of soft tissue, and includes stimuli-sensitive systems with dynamic responses to light and temperature triggers.

"At least one of A and B" should be understood to mean "only A, only B, or both A and B."

"Selected from the group of A, B, and C" should be understood to mean "only A, only B, only C, or both A and B, or both A and C, or both B and C, or A, B, and C."

"At least one selected from one or more of A, B, C, and D" should be understood to mean "only A, only B, only C, only D, or both A and B, or both A and C, or both A and D, or both B and C, or both B and D, or both C and D, or A, B, and C, or A, B, and D, or A, C, and D, or B, C, and D, or A, B, C, and D."

As used herein, an element or step recited in the singular and proceeded with the word "a" or "an" does not exclude plural of said elements or steps, unless such exclusion is explicitly stated. References to an "embodiment" do not exclude the existence of additional embodiments that also incorporate the recited features. Embodiments "comprising," "including," or "having" an element (component, part) or a plurality of elements (components, parts) having a particular property may include additional such elements not having that property. Ordinal numerals or ordinal number words are used as labels, and are not intended to impose numerical requirements or a particular positional order on their objects.

It will be appreciated by persons skilled in the art that the present invention is not limited to what has been particularly shown and described herein above. Rather the scope of the present invention is defined only by the claims which follow.

The invention claimed is:

1. A controlled motion capsule comprising:
a swallowable case,
a controller monitoring at least one data,
a compartment enclosing a shape changing gel,
the shape changing gel comprising a reversible component with at least one hydrophilic component;
the shape-changing gel having an interior material and an outermost layer, the outermost layer having a capacity to protect the interior material;
at least one nonionizing radiation emitter proximal to the shape changing gel;
the controller determining at least one nonionizing radiation value in response to the at least one monitored data;
based on the at least one nonionizing radiation value, the controller variably energizes the at least one nonionizing radiation emitter to at least one level selected from the group of an intensity level and a duration level;
the shape changing gel expanding and contracting to a three-dimensional volume dependent on the at least one level;
wherein motion of the capsule through a tubular structure in an animal is variably decelerated by the expansion and contraction of the shape changing gel.

2. The controlled motion capsule of claim 1, wherein:
the outermost layer comprises an interlocked elastomer.

3. The controlled motion capsule of claim 1, further comprising:
the outermost layer directs the swelling of the shape changing gel in a shape.

4. The controlled motion capsule of claim 1, wherein the shape changing gel expands from a first condition to a second condition in less than 90 seconds.

5. The controlled motion capsule of claim 1,
wherein the shape changing gel remains in a first condition when activated by the nonionizing radiation, and the shape changing gel swells to a second condition when not activated by the nonionizing radiation.

6. The controlled motion capsule of claim 1,
wherein the controller includes a system for determining the controlled motion capsule somalocation.

7. The controlled motion capsule of claim 6,
wherein the controller includes a positioning program;
the positioning program includes at least one feedback mechanism to compute at least one trajectory of the controlled motion capsule;
the at least one feedback mechanism produces at least one duration data selected from one or more of a velocity, deceleration, acceleration, turn, rotation, orientation, direction, slide, and stop duration data;
the positioning program uses the at least one duration data to compute the at least one trajectory;
the controller uses the at least one trajectory to determine the controlled motion capsule somalocation.

8. The controlled motion capsule of claim 6, further comprising:
at least one system that may measure at least one visual, hyperspectral, chemical, physical, or electrophysiological data of the body tubular structure environment;
the controller uses the at least one data to determine the controlled motion capsule somalocation.

9. The controlled motion capsule of claim 6, wherein the shape changing gel maintains the controlled motion capsule in the at least one somalocation for a sufficient time to perform one or more medical tasks.

10. The controlled motion capsule of claim 1, wherein the nonionizing radiation produces a temperature change, and wherein the shape changing gel comprises a thermosensitive soft material.

11. The swallowable capsule of claim 1, in which the shape changing gel comprises a selection from one or more of polymers, liquid crystals, mesogens, resins, or gels, and mixtures thereof.

12. The swallowable capsule of claim 1, wherein the shape changing gel includes:
at least one monomer that includes at least one functional group configured to undergo a reversible photochromic reaction in response to at least one wavelength of nonionizing radiation.

13. The swallowable capsule of claim 1, wherein the shape changing gel includes:
at least one functional group selected from one or more of azobenzenes, diarylethenes, stilbenes, spiropyrans, sulfonated spiropyrans, spirooxazines, spirobenzopyrans, fulgides, dithienylethenes, hexaarylbiimidazoles, azotolene, imines, hydrazones, coumarin, and nitrobenzyl, including moieties, derivatives, and mixtures thereof.

14. The swallowable capsule of claim 1, wherein the shape changing gel further comprises:
a self-healing agent, selected from the group of agents including A) graphene B) acryloyl-6-aminocaproic acid crosslinked with a polymer matrix, and C) dispersed particles that can polymerize a damaged polymer.

15. The swallowable capsule of claim 1, wherein the shape changing gel further comprises:
a liquid crystal elastomer gel in an original shape;
the nonionizing radiation induces a photothermal response in the liquid crystal elastomer gel, thereby changing the shape of the liquid crystal elastomer gel.

16. The controlled motion capsule of claim 1, wherein the shape changing gel expanding is to a three-dimensional volume at least 2 times the volume of the shape changing material when contracted.

17. The controlled motion capsule of claim 1, further comprising:
at least one of a data collecting unit and a data communication unit.

18. The controlled motion capsule of claim 17,
wherein the controller uses at least one data from the at least one of the data collecting unit and
the data communication unit to determine the nonionizing radiation value.

19. A method for inflating and deflating part of a capsule as it passes through a gastrointestinal tube, including:
swallowing the capsule, the capsule comprising:
i) a case having a size that permits swallowing by a human, the case comprising:
1) An area with a controller, the controller variably activating and variably deactivating at least one nonionizing radiation emitter;
2) A compartment storing a gel-like media, including:
a) a first side and a second side opposite the first side;
b) the gel-like media located in the cavity between the sides in a first volume;
c) at least one membrane layer anterior to the gel-like media;
ii) the controller produces at least one first signal to activate the at least one nonionizing radiation emitter;
1) The controller processes at least one first data to determine the at least one first signal;
a) the at least one first data is provided by a source selected from the group of A) at least one sensor included in the capsule, and B) at least one source outside of the body;
2) The at least one nonionizing radiation emitter variably energizes the gel-like media so that it variably inflates to a second volume;
a) the gel-like media inflates through the first and the second sides;
b) the capsule variably decelerates from a cause selected from the group of A) the gel-like media inflation causes interference with peristaltic flow, and B) the gel-like media inflation causes the at least one membrane layer to press against at least one side of the gastrointestinal tube to stop the capsule;
iii) the controller produces at least one second signal to adjust the activation of the at least one nonionizing radiation emitter;
1) The controller processes at least one second data to determine the at least one second signal;
a) the at least one second data is provided by a source selected from the group of A) dynamic feedback of the performance of the capsule over time, B) a predetermined data, and C) at least one source outside of the body;
2) The nonionizing radiation emitter variably energizes the gel-like media to an adjusted volume;
a) the adjusted volume is selected from A) the second volume; B) the first volume; C) a volume between the first and second volumes;
3) The nonionizing radiation emitter de-energizes the gel-like media;
a) the gel-like media and membrane layer deflate;
b) the gel-like media is largely disposed between the first and the second sides.

20. A fail-safe controlled motion capsule, comprising:
the capsule swallowable by an animal;
a shape changing gel enclosed in a container in the capsule;

the shape changing gel variably expanding from an initial state to a three-dimensional volume, in response to nonionizing radiation energy;

a controller;

at least one nonionizing radiation energizer;

the controller variably energizing with nonionizing radiation the shape changing gel;

a first fail-safe system:
   whereby de-energizing of the shape changing gel results in the shape changing gel contracting to the initial state, or substantially close to the initial state, sufficient to allow the controlled motion capsule to pass through a body tubular structure without a problem;

a second fail-safe system:
   a feedback system that detects at least one special case, the at least one special case being the shape changing gel poses a risk to the body tubular structure;
   at least one special compound incorporated in the shape changing gel, wherein if activated the at least one special compound breaks down the shape changing gel;
   the controller, in response to the feedback system detection of the at least one special case, activates the at least one special compound.

* * * * *